US011179140B2

(12) United States Patent
Galluzzo et al.

(10) Patent No.: US 11,179,140 B2
(45) Date of Patent: Nov. 23, 2021

(54) ABLATION TREATMENT DEVICE SENSOR

(71) Applicant: The Technology Partnership Plc, Royston (GB)

(72) Inventors: Paul Mark Galluzzo, Royston (GB); William Henry Gomersall, Royston (GB); Mikhail Evgen'evich Bashtanov, Royston (GB)

(73) Assignee: The Technology Partnership Plc

(*) Notice: Subject to any disclaimer, the term of this patent is extended or adjusted under 35 U.S.C. 154(b) by 472 days.

(21) Appl. No.: 15/319,496

(22) PCT Filed: Jun. 15, 2015

(86) PCT No.: PCT/GB2015/051753
§ 371 (c)(1),
(2) Date: Dec. 16, 2016

(87) PCT Pub. No.: WO2015/193648
PCT Pub. Date: Dec. 23, 2015

(65) Prior Publication Data
US 2017/0156705 A1 Jun. 8, 2017

(30) Foreign Application Priority Data
Jun. 17, 2014 (GB) .................................. 1410743

(51) Int. Cl.
*A61B 8/08* (2006.01)
*A61B 8/12* (2006.01)
(Continued)

(52) U.S. Cl.
CPC ............ *A61B 8/5223* (2013.01); *A61B 8/085* (2013.01); *A61B 8/12* (2013.01); *A61B 8/4483* (2013.01);
(Continued)

(58) Field of Classification Search
CPC ..... A61B 8/5223; A61B 8/485; A61B 8/1492; A61B 8/4483; A61B 8/085; A61B 8/12;
(Continued)

(56) References Cited

U.S. PATENT DOCUMENTS

2002/0115931 A1* 8/2002 Strauss .................... A61B 5/06
600/420
2005/0215899 A1* 9/2005 Trahey ................ A61B 5/0048
600/439
(Continued)

FOREIGN PATENT DOCUMENTS

WO 2013140353 A2 9/2013

OTHER PUBLICATIONS

Chi Hyung Seo et al: "The feasibility of using thermal strain imaging to regulate energy delivery during intracardiac radiofrequency ablation" IEEE Transactions on Ultrasonics Ferroelectrics and Frequency Control IEEE US vol. 58 No. 7 Jul. 2, 2011 Jul. 2, 2011) pp. 1406-1417, XP011329759 ISSN: 0885-3010 DOI:10.1109/TUFFC.2011.1960 abstract figures 1-15 Sections II-IV.
(Continued)

*Primary Examiner* — Carolyn A Pehlke
*Assistant Examiner* — Victoria Fang
(74) *Attorney, Agent, or Firm* — Lerner, David, Littenberg, Krumholz & Mentlik, LLP

(57) ABSTRACT

A treatment device includes a unit having an ultrasound imaging element and an ablation electrode, mechanism for receiving signals from the imaging element, the signals representing plural frames of ultrasound data; and mechanism for processing the signals to provide, in use, at least one of ultrasound data and data indicating mechanical strains within tissue being monitored by the sensor element, the strains being generated by movement of the tissue or the
(Continued)

body being treated, the movement being generated naturally by the tissue or by the device operator's motion, or both.

14 Claims, 8 Drawing Sheets

(51) Int. Cl.
    *A61B 8/00*    (2006.01)
    *A61B 18/14*    (2006.01)
    *A61B 90/00*    (2016.01)
    *A61B 18/00*    (2006.01)

(52) U.S. Cl.
    CPC .......... *A61B 8/485* (2013.01); *A61B 18/1492* (2013.01); *A61B 90/37* (2016.02); *A61B 2018/00577* (2013.01); *A61B 2090/3782* (2016.02)

(58) Field of Classification Search
    CPC ............ A61B 90/37; A61B 2090/3782; A61B 2018/00577
    USPC ........................................................ 600/439
    See application file for complete search history.

(56) References Cited

U.S. PATENT DOCUMENTS

| | | | | |
|---|---|---|---|---|
| 2007/0106157 A1* | 5/2007 | Kaczkowski | .......... | A61B 5/015 600/438 |
| 2008/0081994 A1* | 4/2008 | Kim | .................. | A61B 5/0285 600/438 |
| 2008/0091104 A1* | 4/2008 | Abraham | ............. | A61B 8/0841 600/439 |
| 2008/0285819 A1* | 11/2008 | Konofagou | .............. | A61B 8/08 382/128 |
| 2010/0168569 A1* | 7/2010 | Sliwa | ................... | A61B 8/0841 600/439 |
| 2010/0286518 A1* | 11/2010 | Lee | ....................... | A61B 8/4427 600/439 |
| 2011/0060222 A1* | 3/2011 | Thittai | ................... | A61B 8/485 600/438 |
| 2011/0208038 A1* | 8/2011 | Konofagou | ............ | A61B 5/055 600/410 |
| 2012/0265070 A1* | 10/2012 | Sliwa | ..................... | A61B 8/085 600/439 |
| 2013/0102932 A1* | 4/2013 | Cain | ......................... | A61N 7/00 601/2 |
| 2015/0038842 A1* | 2/2015 | Belt | ...................... | A61B 8/0883 600/438 |
| 2015/0272547 A1* | 10/2015 | Freiburger | ............... | A61B 8/54 600/438 |

OTHER PUBLICATIONS

Stephens D N et al: "Multifunctional catheter's combining intracardiac ultrasound imaging and electrophysiology sensing" IEEE Transactions on Ultrasonics, Ferroelectrics and Frequency Control, IEEE US vol. 55, No. 7, Jul. 2, 2008 (Jul. 2, 2008), pp. 1570-1581, XP011229842, ISSN: 0885-3010, DOI: 10.1109/TUFFC.2008.834 abstract figures 1-6 Sections ll-V.
International Search Report for Application No. PCT/GB2015/051753 dated Sep. 1, 2015.

* cited by examiner

ABLATION TREATMENT DEVICE SENSOR

CROSS REFERENCE TO RELATED APPLICATIONS

This application is a national phase entry under 35 U.S.C. § 371 of International Application No. PCT/GB2015/051753, filed Jun. 15, 2015, published in English, which claims the benefit of the filing date of Great Britain Patent Application No. 1410743.7, filed Jun. 17, 2014, the disclosures of which are hereby incorporated herein by reference.

FIELD OF THE INVENTION

The present invention relates to a sensor for an ablation treatment device.

BACKGROUND OF THE INVENTION

One ailment that is treated with ablation is atrial fibrillation (AF). AF is associated with unwanted electrical conduction pathways in the heart, causing erratic heart beating. AF is treated by radiofrequency (RF) ablation, whereby electric current is passed through heart wall muscle tissue, leaving behind necrotic (ablated) tissue thereby stopping the electrical conduction pathway in that tissue. The RF ablation is of course performed selectively, such that only selected zones of the heart are ablated, rather than the entire heart.

Said ablation is most commonly performed with a catheter which is passed into the heart via the aorta, or an endoscope which is used epicardially. In a common embodiment, a radiofrequency (RF) ablation catheter is unipolar, i.e. it has one or more active electrodes in the distal tip of the catheter and an Earth pad attached to the patient's skin elsewhere. Current flows from the tip to the Earth pad, and the current density is greatest near the catheter tip, and hence the ablation caused by Ohmic heating is greatest near the tip. Bipolar devices also exist, whereby current flow between two electrodes located at the distal tip of the catheter. In some devices, saline is pumped through small holes in the distal tip of the catheter, to cool the surface of the tissue and cause the hottest part of the tissue to be slightly below the surface.

A key problem faced by electrophysiologists who use these ablation devices is that they do not know the depth of the RF ablation lesion relative to the local thickness of the heart wall. On one hand, inadequate ablation may fail to permanently treat the AF and the patient may need another ablation procedure. On the other hand, excessive ablation can be lethal if the RF ablation effect extends to nearby organs. Hence there is a desire to understand the depth of the RF ablation lesion, in particular to know whether it extends all the way through the full thickness of the heart wall (i.e., is transmural). Hence the overall problem in electrophysiology is to create a "transmurality sensor".

Other methods of destroying tissue for the treatment of atrial fibrillation and other ailments include cryo (freezing), laser ablation, chemical and high intensity focused ultrasound (HIFU). However, as with RF ablation, there is no method currently for adequately monitoring and assessing the lesion formation. Examples of other ailments treated with ablation include:

Ablation of tumours in the lung, liver, kidney and bones, as well as other body organs.

Cardiology: atrial flutter, supraventricular tachycardia (SVT), atrial tachycardia and some types of ventricular arrhythmia (in addition to atrial fibrillation).

Renal denervation: ablation of nerve endings in the renal arteries to treat cases of cases of 'resistant hypertension' (defined as blood pressure readings over 150/90 despite three antihypertensive medications)

Varicose Vein Ablation

Somnoplasty, to treat obstructive sleep apnea by ablating (and hence reducing volume of) the soft palate Endometrial ablation for the treatment of menorrhagia (heavy periods), i.e. ablating the endometrial cells of the uterus Uterine Fibroid Ablation Pain management: ablation of nerves responsible for transmission of pain signals to brain Treatment of Barrett's esophagus, by ablating the esophagus. Barrett's esophagus is believed to be a reaction to chronic acid exposure, which is found in a significant number of patients who present heartburn to their doctor, and which is believed to be a pre-cursor to esophageal cancer.

Arthroscopic ablation of, for example, joint surfaces—see for example U.S. Pat. No. 7,481,807 B2

Ablation of pathologic tissue associated with tendonopathies such as lateral epicondylitis (tennis elbow)

Treatment of chronic total occlusion of blood vessels

Removal of plaque from blood vessels, for example in an atherectomy procedure

A number of approaches to sensing the depth of the ablation lesion to determine if it is transmural have been proposed.

Optical imaging approaches that have been explored include optical coherence tomography (OCT) and photoacoustic imaging. An example publication in the latter area is US 20100280504. However, due mainly to optical scattering, optical imaging methods are unable to provide sufficient image depth to see through the full thickness of a typical atrial wall. Optical techniques have a further disadvantage, in that tissue surface charring can partially blind an optical sensor by blocking light penetration through the tissue surface.

Electrical impedance approaches have been explored, see for example U.S. Pat. No. 7,192,427. Others have attempted to estimate the lesion depth based on temperature measurements at the surface, for example EP1818021. However, these methods do not provide a spatial scan or image, and hence are limited in their breadth of applicability.

Ultrasound imaging offers spatial information at depths which are commensurate with the thickness of the heart wall, and this method has been pursued also because ultrasound scanning probes can be made at small scale and at low cost. Whilst intracardiac echo ultrasonic phased-array imaging probes (ICE probes) are difficult to align with ablation devices, and are relatively expensive, prior art such as US 2012/0004547 and US 2012/0265069 offer combined ultrasound imaging and RF ablation capabilities.

In US 2012/0004547, an ultrasound scan of the heart wall is produced, and analysed to identify the depth of the lesion and the depth of the heart wall. An ultrasound scanning function is integrated with an endocardial ablation catheter or epicardial ablation device. One technique employed in the prior art is to look for differences in echogenicity in the heart wall, seeking to differentiate the lesion from the surrounding tissue based on a discontinuity in the ultrasound image, such as a transition between hyperechoic to hypoechoic regions. Another technique described is to look for swelling (oedema) in the heart wall by looking at the long term physical distortion of regions of the tissue by cross-correlating regions of the image with regions of previous images, and to estimate the depth of the lesion by associating a measured depth of oedema with the actual depth of the lesion. The nature of that cross-correlation technique is to track large changes (on the order of a millimetre) in the location of features of the data over the course of the longer term ablation (tens of seconds), rather than evaluating lesion depth solely based on relatively instantaneous small physical distortions (on the order of microns when plotted against depth) in the signal over short time scales (less than a second). A related approach is taken by US 2012/0265069, whereby a carbon-based window between the ultrasound transducer and the tissue provides a combination of acoustic and electrical properties, to facilitate an improved ultrasound imaging/RF ablation combination device.

The approach proposed in US 2012/0004547 and US 2012/0265069 requires recognition of features (in particular the lesion) in an ultrasound image: either through echogenicity or long term swelling. The problem with this approach is that it suffers from a lack of specificity, in that the lesions are not universally visible in the ultrasound image. For example echogenicity differences are sometimes imperceptible, and oedema associated with ablation can be variable and sometimes impractical to identify.

Whilst RF ablation lesions are sometimes invisible with ultrasound alone, they are generally palpable, so one improvement to US 2012/0004547 is to exploit variations in physical stiffness through the use of ultrasonic elastography. In ultrasonic elastography, successive ultrasound scans of the same tissue are analysed to produce a map of physical stiffness throughout the tissue. Acoustic Radiation Force Imaging (ARFI) based ultrasonic elastography has been proposed as a means of evaluating lesion depth, and operates on the basis of applying an acoustic force to the tissue, cross-correlating features between successive frames of the ultrasound data while the force is varied, calculating the amount of physical displacement of those features due to the acoustic force, and evaluating physical stiffness throughout the tissue based on either strain (the slope of displacement with position, i.e. d(displacement)/dz) or shear wave velocity (rate of propagation of lateral waves with distance).

Prior art on the use of ARFI imaging to detect lesion depth includes US20050215899. In that prior art, the first ultrasound image is generated with a first "tracking pulse", the force is applied with a higher energy "pushing pulse", and the second ultrasound image is generated with a second "tracking pulse". The downside of this prior art is that it involves a complex imaging array (one dimensional or two dimensional) and requires the "track-push-track" sequence.

In typical ultrasonic elastography systems, lateral correlations are used to enhance the quality of axial displacement measurements. This requires two (or three) dimensional ultrasound image data, and in the US20050215899 prior art this is achieved through the use of a one (or two) dimensional ultrasound scan array probe.

The premise of elastography is to deduce the mechanical stiffness throughout the tissue, by comparing the displacement of features between successive frames of ultrasound imaging, and hence to compute strain or shear wave velocity, which are each related to mechanical stiffness. For this computation to be at its most accurate, the preferred magnitude of displacement of features from frame to frame is a fraction of an acoustic wavelength, because this enables the highest quality of detailed feature tracking. For example with 15 MHz imaging the acoustic wavelength is approximately 100 μm, so it is preferable for features in the ultrasound scan to shift by around 10 μm between successive frames.

In the ARFI prior art a "push pulse" is used to generate tens of microns of displacement, and in other elastography systems the user manually applies force to the patient's body to cause mechanical displacement. With these systems an array probe with multiple elements (for example 128 elements) is used to detect displacements, relying on lateral correlations for the purpose of the elastography analysis. In theory it would be preferred to use a single element ultrasound scanner due to the reduced complexity of both hardware and electronics, but a single element which generates a 1D image can not utilise lateral displacement of scatterers because we only have a single axially-oriented signal (A-line) of information, rather than multiple "A-lines" which enable lateral correlations. Hence a single element would be reliant upon tracking only the axial component of displacement of features in a single A-line, and the sub-wavelength displacement becomes particularly important. So such devices are inherently complex and/or require considerable skill of operation to generate displacement reliably and accurately. Here, "axial direction" is referring to the depth direction relative to the ultrasound element.

Accordingly there is a need to produce an accurate sensor for determining ablation treatment results that is of low cost, and simple to operate.

BRIEF SUMMARY OF THE INVENTION

According to the present invention, there is provided a treatment device comprising: a frame retaining an ultrasound imaging element and an ablation electrode; means for receiving signals from the imaging element, the signals representing plural frames of ultrasound data; and means for processing the signal to provide, in use, at least one of ultrasound data and data indicating mechanical strains within tissue being monitored by the sensor element, said strains being generated by natural movement of the tissue or the body being treated.

The patient's body's own movement, such as the heart's own beating [or the lung's respiration if working with lungs] causes displacement of speckle features in directions including the axial direction, so the inevitable motion of such organs (heart or lung) is analysed by an elastography data processing algorithm to deduce a distribution of strain. Regions of low strain are associated with either high stiffness or low contraction, and both of these effects are of interest for clinical purposes. For example: a stiff region which suppresses the magnitude of axial strain can be associated with an RF ablation lesion, or other object of interest such as a tumour. Alternatively, a region of heart muscle or other tissue which is failing to contract or expand due to ablation-induced necrosis, and which is consequently suppressing the magnitude of strain, can also be associated with an RF ablation lesion. Either of these is sufficient, and both have the same effect and hence work in tandem. Hence the first aspect of our solution is to rely upon the axial component of displacement caused by the body's (such as the heart's or lung's) own motion, and use an elastography data processing algorithm to deduce the distribution of mechanical strain, and hence infer the distribution of stiffness, necrosis or other relevant property. This measurement approach is capable of detecting low strains in lesions associated with either (a) higher elastic stiffness, or (b) lack of muscle contraction.

BRIEF DESCRIPTION OF THE DRAWINGS

Examples of the present invention will now be described with reference to the accompanying drawings, in which.

DETAILED DESCRIPTION

The present invention integrates the ultrasound imaging probe with an RF ablation electrode. This can either use the electrode itself as the probe's acoustic matching layer (hence serving a dual purpose), or the electrode can be acoustically transparent (hence avoiding degradation to the signal to noise ratio), or the electrode may contain a small gap in front of the probe. It is very convenient to combine ablation and imaging functions in a single device, particularly as it ensures that the image is aligned with the RF ablation lesion, rather than having to find the lesion with a separate tool. This is shown in FIGS. 4A-4C.

Figure 1:
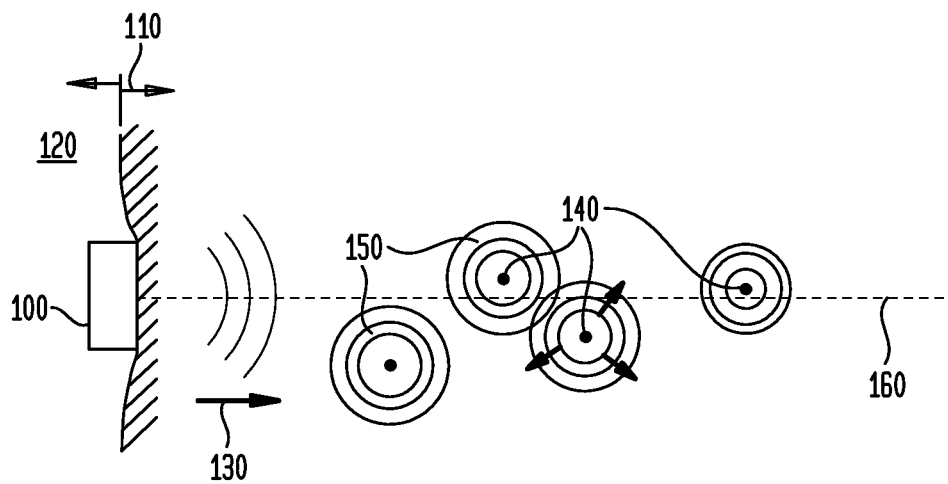
FIG. 1 is a schematic drawing showing operation of a sensor according to the present invention.
Figure 2:
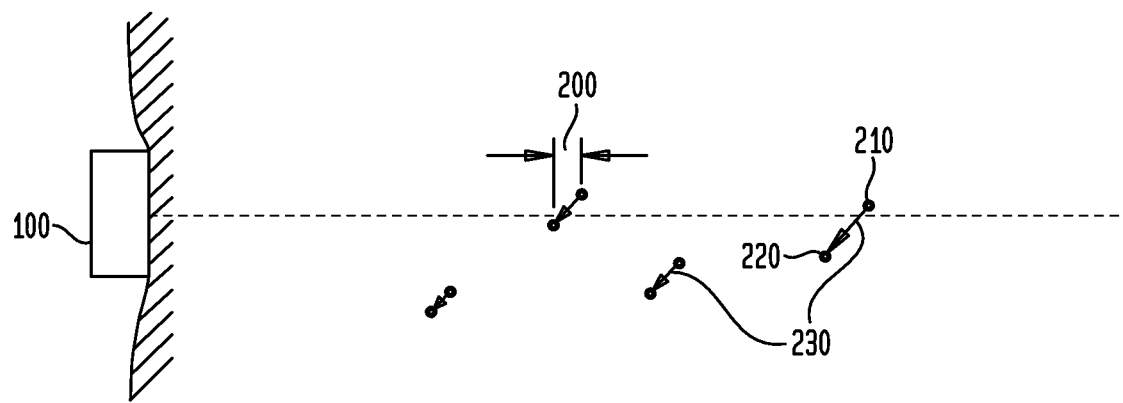
FIG. 2 is a schematic drawing showing the axial component of tissue displacement.
Figure 3:
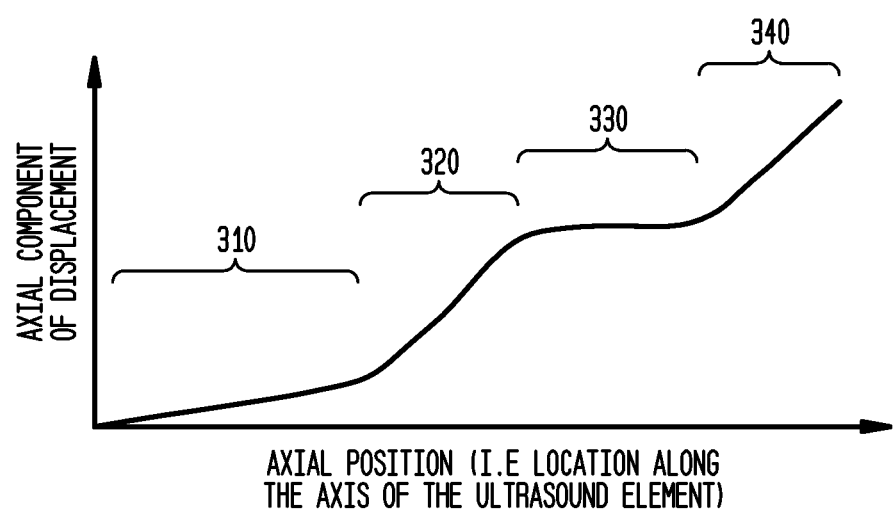
FIG. 3 is a an example of a one-dimensional displacement map generated by a single element device, illustrating how the axial component of displacement (whose slope equals the axial component of strain) may vary with respect to axial position, whereby axial position is defined as the distance from the ultrasound imaging element along its axis.

FIG. 1 illustrates a probe assembly 100 containing an ultrasound element arranged against a tissue 110, (e.g., a heart wall) in an accessible region 120 (e.g., endocardial blood). The probe assembly may emit ultrasound pulse 130 along an axis 160 of the ultrasound element. FIG. 1 further includes features 140 of tissue which scatter the ultrasound pulse and scattered waves 150. FIG. 2 illustrates displacement 230 of the features of tissue, e.g., from an old position 210 to a new position 220 and an axial component 200 of the displacement along the axis 160. FIG. 3 illustrates various axial components of displacements as a function of the axial position, where a segment 310 represents medium strain, a segment 320 represents high strain, a segment 330 represents low strain, and a segment 340 represents high strain.

Figure 4A:
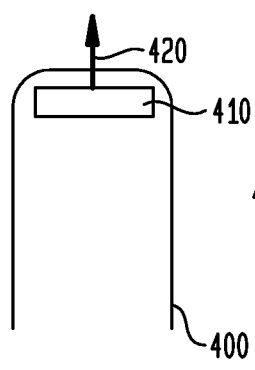
FIGS. 4A-4C are schematic drawings showing the alternative probe configurations.
Figure 4B:
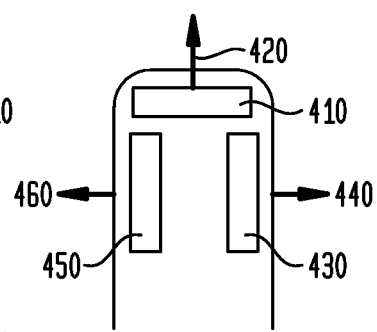
Figure 4C:
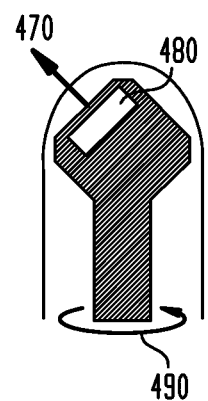

FIG. 4A shows a probe 400 with an axial element 410 having an imaging direction 420. A further optional aspect of our proposed solution is to include more than just one ultrasound imaging element. In an example configuration, one such element may be oriented axially and others may be oriented radially. This is shown in FIG. 4B which illustrates a first radial element 430 having an imaging direction 440 and a second radial element 450 having an imaging direction 460. The advantage of including more than one ultrasound imaging element is that it offers multiple viewing angles, and the user would be expected to use information from the viewing angle which is most close to being orthogonal to the plane of the tissue surface.

Figure 6:
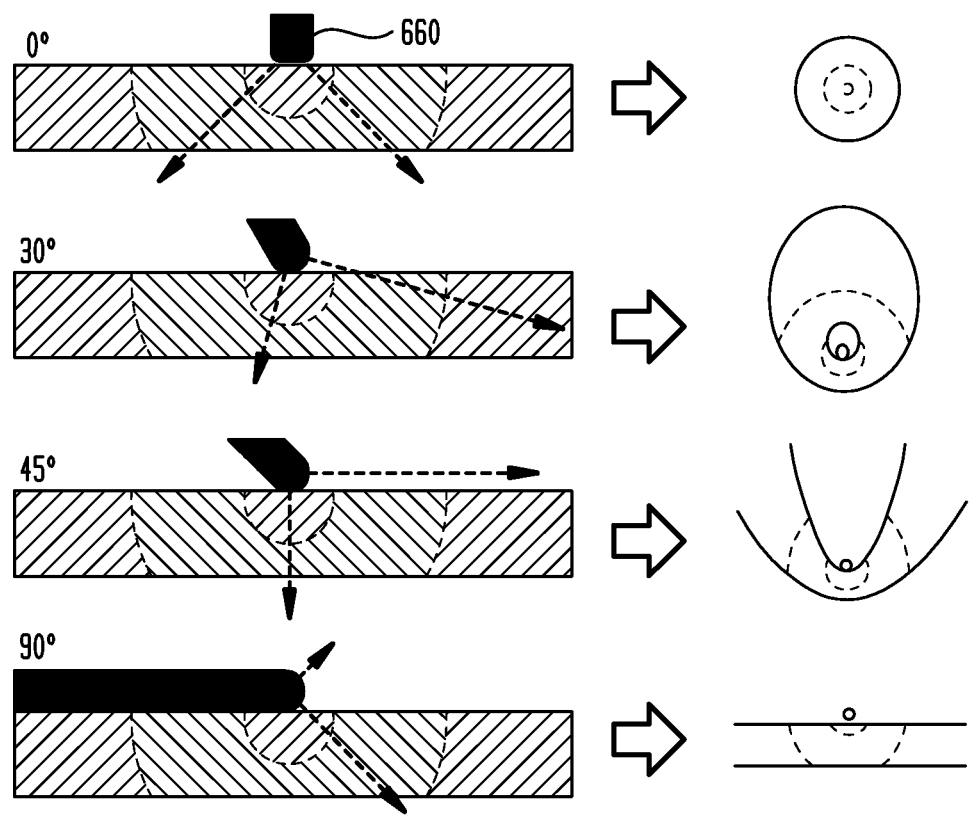
FIG. 6 is a schematic drawing showing the location of a device according to the rotating element embodiment of the present invention with the element angled at 45 degrees relative to the axis of the device, at different relative angles to the surface of a body tissue, with indications of the boundaries between discernable regions of strain images or ultrasound images that may be generated. This illustrates that clinically important geometry is still discernable with the angled rotating element embodiment regardless of the angle between the tissue and the device.

A yet further optional aspect of our proposed solution is to vary the imaging direction of the single element, either through mechanical rotation of the element itself, or through the use of a variable acoustic lens/mirror. Rotating single element ultrasound imaging systems are well known in the art, but they typically view in a radial direction, orthogonal to the axis of a narrow catheter housing the element. In our case, we locate the imaging element 480 at the distal tip of the catheter, pointing at a fixed angle such as in an imaging direction 470 that is 45 degrees between the radial and axial directions, and rotate it about the axial direction as shown by arrow 490. This is shown in FIG. 4C. By keeping the angle of inclination of the imaging element relative to the axial direction between 0 degrees and 90 degrees, the imaging vector sweeps the surface of a cone ("imaging cone"). The advantage of this arrangement, particularly if the angle of inclination is fixed at a mid-range value such as 45 degrees, is that more information is obtained about the shape and depth of the lesion than in the case of one static imaging element, because the surface of the imaging cone bisects the edge of the RF ablation lesion at a range of locations, permitting a greater range of ultrasound image and mechanical strain information to be acquired. A further advantage of this arrangement is that the user can be more flexible with regards to the angle of impingement between the device and the surface of the tissue: with a single fixed element the user should ideally bring the device into contact with the tissue such that the axis of the single fixed imaging element (or of at least one fixed imaging element if the device contains a plurality of fixed imaging elements) of the device is within approximately 45° of a direction normal to the local surface of the tissue; whereas an "imaging cone" can be arranged such that at least some of the imaging cone is within 45° of the direction normal to the local surface of the tissue, regardless of the angle between the device and the tissue. This is illustrated in FIG. 6, at four different device/tissue impingement angles. In this arrangement the generation of elastography data (i.e. the calculation of mechanical strains) is optional, because in this novel arrangement, the ultrasound image data itself is useful in its own right.

In FIG. 6 the features on the left-hand images are as follows, for the left-hand images: Solid Black Area: a tip of a device 660, containing a 45°-angled rotating element whose imaging direction sweeps the surface of a cone, Hashed Areas: tissue, Different Hash Directions: different levels of ablation/lesion depths, Thick Dashed Arrows: edge of "imaging cone", Solid Lines: top and bottom surfaces of tissue, Dotted Lines: boundary of ablation lesion, for two different levels of ablation.

The key for the right-hand images shows, as a solid black area, the area behind the imaging element, and for the solid and dotted lines these correspond to the solid and dotted lines of the left-hand images. The left-hand images show four different catheter/tissue impingement angles where the out of plane angle is 0 in all cases. As can be seen from the right-hand Figures, boundaries of regions in the corresponding ultrasound and/or strain images from the catheter are shown, illustrating how the edge of the lesion and the surface of the tissue may be identified for the different catheter/tissue impingement angles.

Figure 5A:
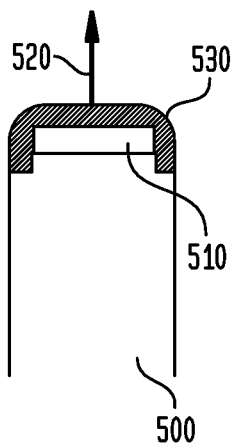
FIGS. 5A-5D are schematic drawings showing key elements of a combined sensor and ablation device according to a number of examples of the present invention.
Figure 5B:
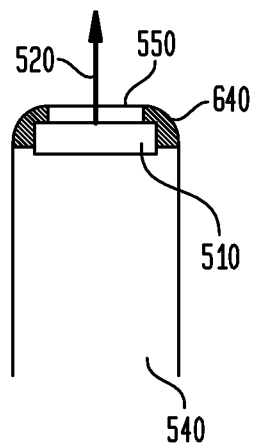
Figure 5C:
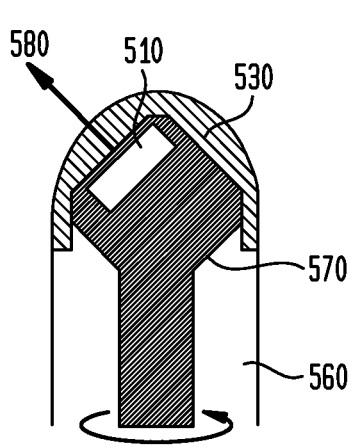
Figure 5D:
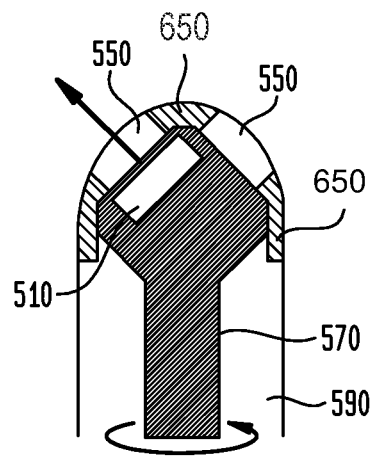

FIG. 5A illustrates a combined sensor and ablation device 500 with an ultrasound imaging element 510 having an imaging direction 520. Silver loaded epoxy 530 may act as both acoustic matching layer and an RF ablation electrode. FIG. 5B illustrates a combined sensor and ablation device 540, which is similar to the device 500 and additionally includes a "window" 550 for imaging and either a ring electrode or two linear electrodes 640. FIG. 5C illustrates a combined sensor and ablation device 560 having a rotating element 570 with an ultrasound imaging element 510 having an imaging direction 580 and silver loaded epoxy 530 which may act as both an acoustic matching layer and an RF ablation electrode. Finally, FIG. 5D illustrates a combined sensor and ablation device 590 similar to the device 560 except an imaging "windows" 550 and ablation electrodes 650.

The present invention employs an elastography data processing algorithm. For a given ultrasound imaging element, the algorithm used for evaluating the axial component (in the frame of reference of that imaging element) of physical displacement based upon ultrasound data is as follows:

1. With the ultrasound imaging element pointing in substantially the same direction and with the probe making contact with substantially the same tissue and at substantially the same location and angle, a number (two or more) of 1D ultrasound frames (or "A-lines") are obtained. The method of generating each 1D ultrasound frame is to send one or more ultrasound pulses out through the tissue, receiving dynamic echoes after the ultrasound pulses have been scattered within the tissue, and generating the 1D ultrasound frame based on the detected dynamic echoes from at least one of the one or more ultrasound pulses.
2. The most recent (at least two) such dynamic echo responses are stored, whereby the tissue is considered to be in an initial position in the first such dynamic echo response, and in displaced position(s) in the subsequent such dynamic echo response(s).
3. Physical displacement is evaluated by analysing the changes in signal between the two or more dynamic echo responses. Methods of analysing changes in signal between ultrasound frames include cross-correlation (see for example Greenleaf, Chen and Song WO2014055973 A1), time-to-peak (see for example Greenleaf, Chen and Song WO2014055973 A1), or signal phase difference (see for example Lindop and Treece, GB 2438461 A) amongst others.
4. Mechanical strain values are optionally calculated, based on the rate of change of physical displacement with axial position, and an image of the same mechanical strain values is optionally displayed.

The level of displacement associated with the heart's (or lung's) motion is generally far in excess of a fraction of an acoustic wavelength in an ultrasound device. In the case of a beating heart for example, the rate of displacement may be of the order of millimetres per second, and typical ultrasound imaging is undertaken at tens of frames per second, hence the displacement from frame to frame is typically of the order of hundreds of microns or more. That high level of displacement often cause glitches in the elastography data analysis algorithm, but by operating with a single element we can massively increase the frame rate whilst still exploiting a standard level of electronics. For example, operating at 3,000 frames per second, we typically ensure that the maximum displacement from frame to frame never exceeds 10 μm. Hence a further aspect of our invention is to operate the ultrasound imaging device with a very high frame rate (e.g. more than 100 frames per second or in the range of 300 to 5000 frames per second). A further benefit of this single element system is the resultant low cost of the device, which can hence be commercially acceptable as a single-use disposable device.

Figure 7:
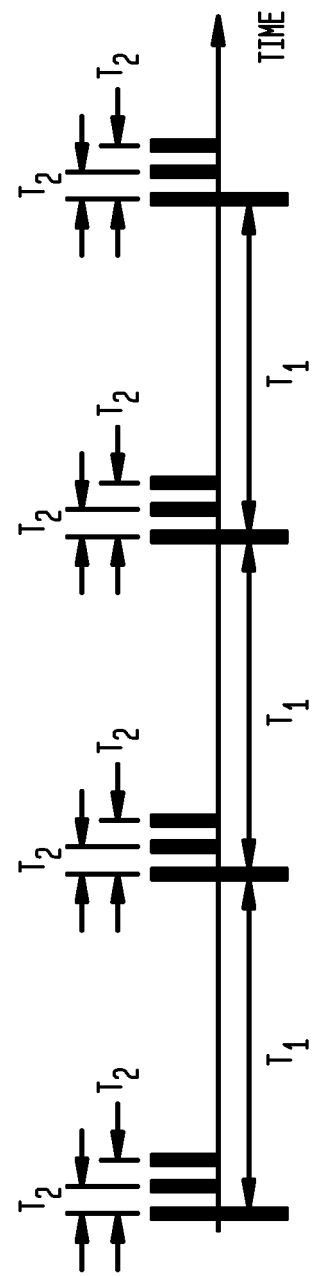
FIG. 7 is a diagram showing the timings of ultrasound frames that may be used in an example of the present invention.

Optionally, the high frame rate can be sustained only for the period of time required to acquire the two or more frames of ultrasound data required to generate one single elastographic (mechanical strain) measurement. FIG. 7 shows a signal representing the bursts of ultrasound data that may be generated with the device of the present invention. Period T2 represents individual high frame required to acquire the two or more frames of ultrasound data to generate the appropriate measurement. T1 shows the time separation between those measurements. In this way, the time separation of the two or more frames of ultrasound data required to generate one single elastographic measurement (T2) could be as short as 100 microseconds, whereas the ultrasound image frame rate (T1) is typically 30 milliseconds per frame (33.3 frames per second).

In cases where the magnitude of displacements is low, the time separation of the two or more frames of ultrasound data required to generate one single elastography measurement (T2) may need to be longer than the desired time separation of ultrasound image frames (T1), to achieve a reasonable level of displacement signal by allowing displacement to build up for a longer time between ultrasound frames. In such a case the ultrasound image frame rate (T1) may either be slowed down to equal the time separation of the two or more frames of ultrasound data required to generate one single elastography measurement (T2), or alternatively the two or more frames of ultrasound data required to generate one single elastography measurement may be chosen as a subset of recent ultrasound frames instead of slowing down the ultrasound frame rate (in which case T2 would be an integer multiple of T1).

Figure 8:
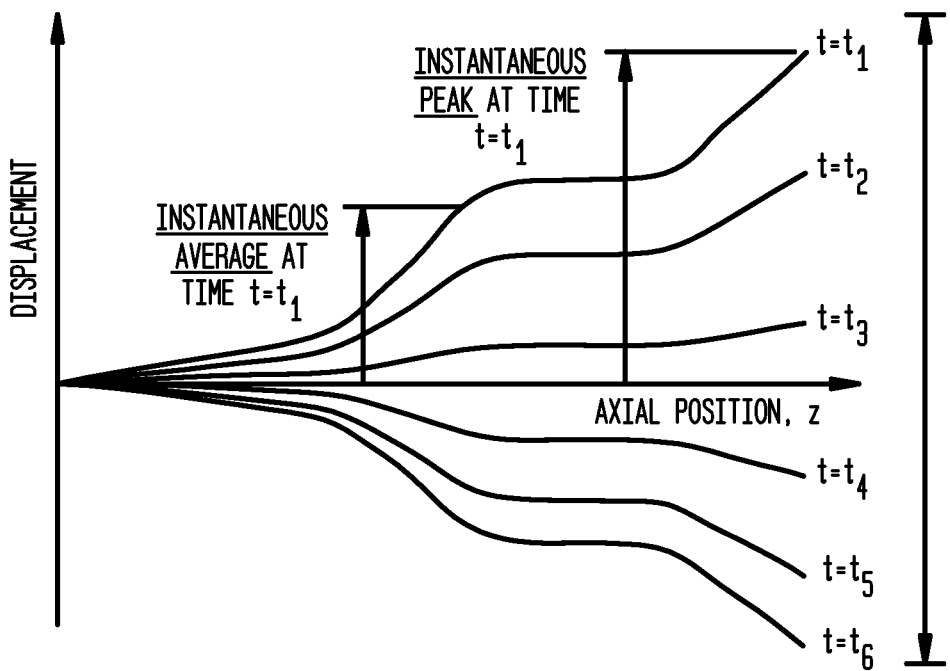
FIGS. 8-13 are a series of graphs showing the steps that may be used to analyse the received ultrasound data from the system of the present invention to provide an output to a user.
Figure 9:
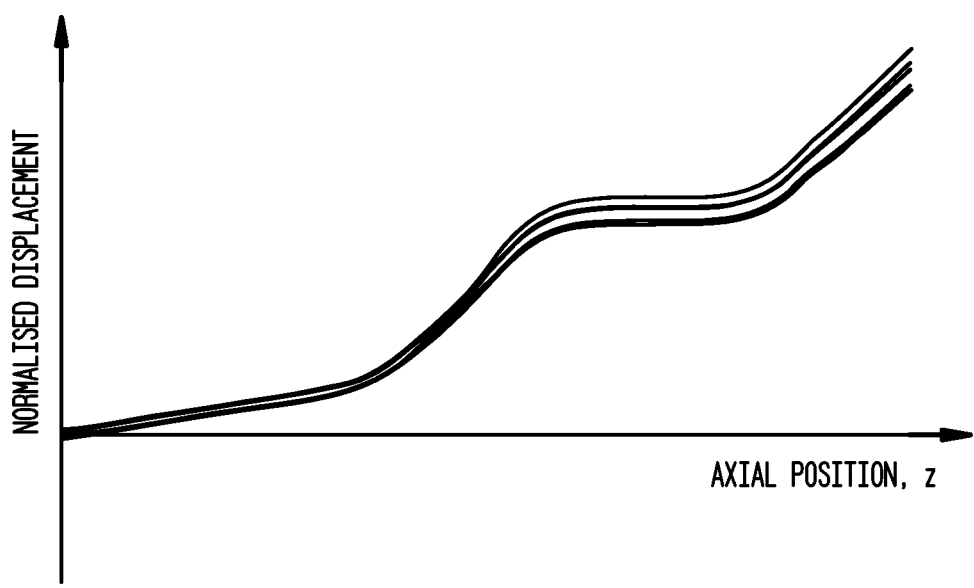

With all of the examples described above the received data can be processed and analysed to provide clear and readily understandable information to an end user. As shown in FIG. 8, the ultrasound data can be used to calculate instantaneous displacement with respect to the axial position of the unit of the invention. The calculated displacements can then be normalised as shown in FIG. 9, and then averaged to compensate for noise in each displacement measurement. Here normalised instantaneous displacements are calculated by dividing instantaneous displacements by instantaneous peak (or by instantaneous average, or a multiple thereof). This normalisation and averaging provides clearer and more accurate information to an operator to ensure an accurate understanding of displacement is provided to ensure accurate operation of any treatment component of the device. It will be appreciated that a similar normalisation and averaging process can be performed on calculated strain measurements instead of displacements to achieve a similar objective.

Figure 10:
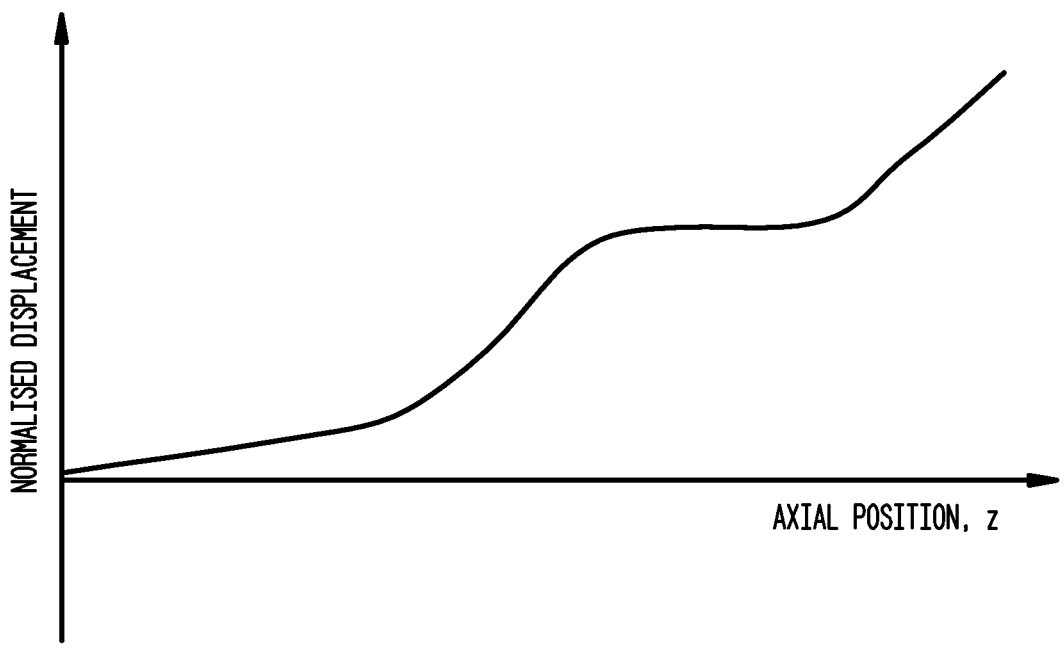

In FIG. 10 the average normalised displacement is shown and this is calculated by averaging the normalised instantaneous displacements.

The normalisation can be carried out by dividing calculated mechanical displacement by the average or peak instantaneous mechanical displacement and then carrying out an averaging of recent normalised instantaneous mechanical displacements to compute a time-averaged normalised mechanical displacement.

With such an approach, the time averaged normalised mechanical displacement can be scaled by multiplying them by the magnitude of variation of displacement associated with the motion or movement of the operator (reflected by movement of the unit), or with a combination of both, to compute scaled time-averaged mechanical displacements. Whereas the normalisation process hides the absolute values of displacement, the purpose of the scaling process is to restore a quantitative measurement capability. Thus, this scaling process provides an ability to distinguish strain images based on the overall magnitude of strain, rather than just the normalised pattern of strain. This is applicable for example for distinguishing fully transmural RF ablation lesions in the heart, from extremely thin (or absent) RF ablation lesions: the strain profile may be uniform in both cases such that they appear similar after the normalisation process, but the magnitude of strain is suppressed in the ablated case such that it is distinguishable after the scaling process.

Figure 11:
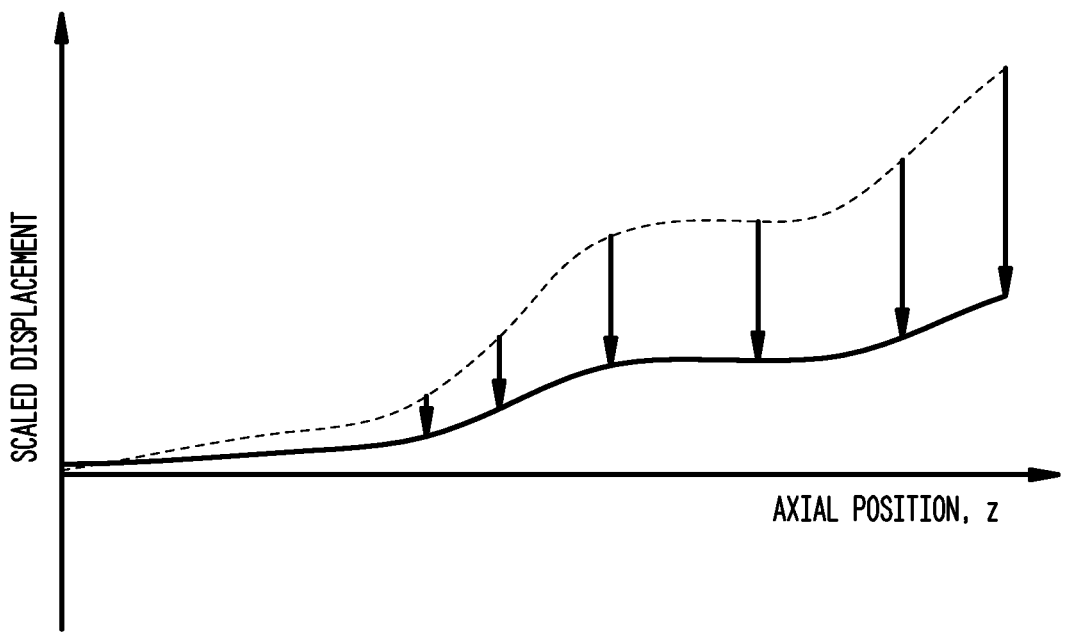
Figure 12:
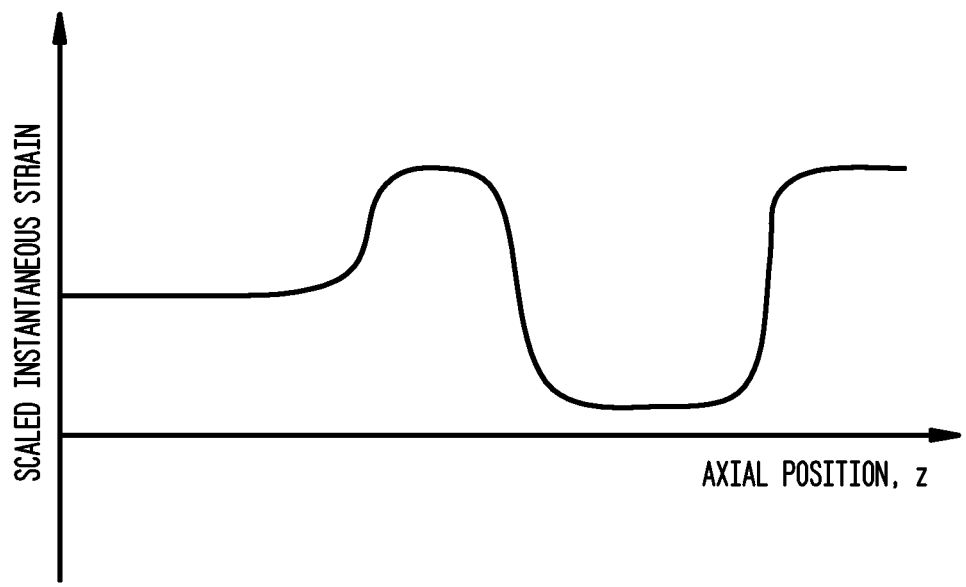

FIGS. 11-12 show how displacement values can be differentiated to provide an indication of strain to provide yet further information to an operator. With such an approach to providing strain output there may be scaling of the displacement data prior to differentiation, or scaling of the strain data after differentiation.

In FIG. 11 scaled average normalised displacement is calculated by multiplying the average normalised displacements by the magnitude of the instantaneous displacements (or by a multiple thereof).

In FIG. 12 the scaled average normalised strain is calculated as the gradient (rate of change with respect to axial position) of scaled average normalised displacement. Then, in FIG. 13 there is shown, in cases where tissue is being distorted by adjacent motion, rather than under its own contraction, relative stiffnesses, which are estimated by inverting the strain.

Figure 13:
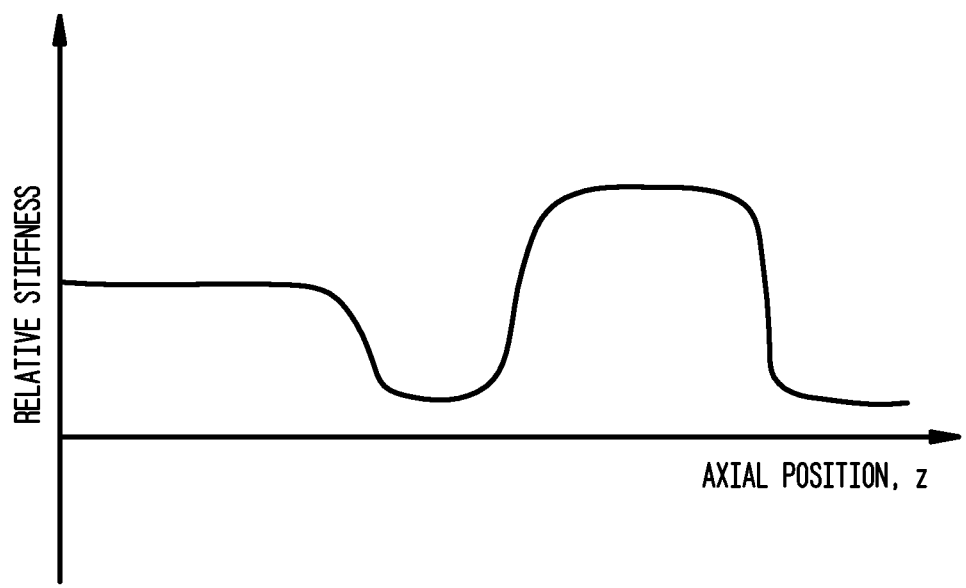

FIG. 13 shows how calculated values of strain may be inverted to provide an estimate of the relative stiffnesses in the strain image. This is particularly helpful in cases where the strain is not caused by natural motion of the tissue in the strain image, for example in cases where the strain is caused by the motion of the operator's hand or by surrounding tissue.

As will be appreciated from the above, the system can be configured to provide, for each ultrasound imaging element, a display of scaled time-average mechanical strains that are displayed both as a function of time and axial position. Furthermore the system can display scaled time-averaged mechanical strains as a function of depth and/or scaled time-averaged displacements as a function of depth. It is also possible for the system to provide time-average normalised displacements as a function of depth. All of these features then enable more accurate treatment to be performed.

With any of the embodiments described of the present invention, the ultrasound data can be used in its own right to determine the location of important anatomical features, in addition to being used for the purpose of elastographic calculations. Such anatomical features may include for example the distance from the device to the near and far edges of the tissue being ablated, the presence of nearby organs and the distance from such nearby organs.

With the present invention it is possible to provide a low cost device which is simple to operate yet which improves significantly the quality and accuracy of information that can be provided to a user.

The invention claimed is:

1. A treatment device comprising:
  a probe comprising an ultrasound imaging element and an ablation electrode; and
  one or more processors associated with the probe,
  wherein the treatment device is configured to operate at a predetermined number of frames per second such that a maximum displacement from frame to frame of a tissue or a body being treated does not exceed a predetermined threshold,
  wherein the treatment device is configured such that the predetermined number of frames per second is sustained only for a period of time required to acquire two or more frames of ultrasound data required to generate a single elastographic measurement,
  wherein at least one of the one or more processors is configured for receiving signals from the ultrasound imaging element, the signals representing frames of ultrasound data at the predetermined number of frames per second of 300 frames per second or more; and
  wherein at least one of the one or more processors is configured for processing the signals to provide, in use, at least one of ultrasound data and data indicating mechanical strains within tissue being monitored by the ultrasound imaging element, said mechanical strains being generated by a movement of the tissue or the body being treated, the movement being generated naturally by the tissue or by a motion of an operator of the treatment device, or naturally by the tissue and by the motion of the operator of the treatment device.

2. The treatment device according to claim 1, wherein the predetermined number of frames per second is 300 or more while obtaining the frames of ultrasound data required for each mechanical strain calculation, or less than 100 frames per second at other times.

3. The treatment device according to claim 1, wherein:
  at least one of the one or more processors is configured to calculate instantaneous mechanical displacements or strains as a function of an axial position of the unit based on the received signals representing frames of ultrasound data; and
  at least one of the one or more processors is configured for normalising the calculated instantaneous mechanical displacements or strains.

4. The treatment device according to claim 3, wherein the at least one of the one or more processors configured for normalising is configured to normalise by dividing one of the calculated instantaneous mechanical displacements or strains by a magnitude of instantaneous mechanical displacement or strain at that instant, respectively, where the magnitude is represented by a multiple of the average or peak with respect to the axial position at that instant, and calculating a moving average with other recent normalised calculated instantaneous mechanical displacements or strains, to compute time-averaged normalised calculated mechanical displacements or strains.

5. The treatment device according to claim 4, configured such that the time-averaged normalised calculated mechanical displacements or strains are scaled by multiplying by a magnitude of variation of displacement or strain associated with the body's own motion or with the movement of the operator or with both, where the magnitude is represented by a multiple of the peak-to-peak variation with respect to time at a fixed axial position, to compute scaled time-averaged mechanical displacements or scaled time-averaged mechanical strains.

6. The treatment device according to claim 4, further configured such that the scaled time-averaged mechanical strains are calculated as the rate of change of time-averaged mechanical displacements with respect to the axial position.

7. The treatment device according to claim 3, configured such that, for the ultrasound imaging element, scaled time-averaged mechanical strains are displayed as a function of both time and axial position, and/or scaled time-averaged mechanical strains are displayed as a function of depth, and/or scaled time-averaged mechanical displacements are displayed as a function of depth, and/or the time-averaged normalised displacements are displayed as a function of depth.

8. The treatment device according to claim 3, wherein the at least one of the one or more processors configured for processing the signals is configured to use a cross-correlation algorithm, a time-to-peak algorithm or a signal phase difference algorithm on the frames of ultrasound data to compute the calculated instantaneous mechanical displacements or strains.

9. The treatment device according to claim 3, wherein the at least one of the one or more processors configured for processing the signals is further configured to determine levels of stiffness, magnitudes of muscle contraction and/or tissue types within the tissue based upon the calculated instantaneous mechanical strains.

10. The treatment device according to claim 1, comprising plural ultrasound imaging elements.

11. The treatment device according to claim 10, wherein one of the plural ultrasound imaging elements is arranged in an axial direction and at least one other of the plural ultrasound imaging elements is arranged in a radial direction.

12. The treatment device according to claim 10, wherein the plural ultrasound imaging elements and the ablation electrode are rigidly retained to one another by a frame.

13. The treatment device according to claim 1, wherein the ultrasound imaging element is arranged on a rotating component and is aligned in a direction offset from the axis of rotation of the rotating component.

14. The treatment device according to claim 1, configured to further provide the ultrasound data to the operator of the treatment device.

* * * * *